United States Patent [19]

Monn et al.

[11] Patent Number: 5,196,415
[45] Date of Patent: Mar. 23, 1993

[54] 5-AMINOCARBONYL-5H-DIBENZO[A.D]CYCLOHEPTEN-5,10-IMINES FOR TREATMENT OF EPILEPSY AND COCAINE ADDICTION

[75] Inventors: James A. Monn, Gaithersburg; Andrew Thurkauf, Crofton; Shunichi Yamaguchi, Bethesda; Michael A. Rogawski, Columbia; Kenner C. Rice, Bethesda; Mariena V. Mattson, Rockville; Arthur E. Jacobson, Potomac, all of Md.

[73] Assignee: The United States of America as represented by the Department of Health and Human Services, Washington, D.C.

[21] Appl. No.: 827,383

[22] Filed: Jan. 29, 1992

Related U.S. Application Data

[62] Division of Ser. No. 349,187, May 9, 1989, abandoned.

[51] Int. Cl.$^5$ .................. C07D 221/22; C07D 223/10; A61K 31/44; A61K 31/55
[52] U.S. Cl. .................................. 514/210; 514/212; 514/286; 540/362; 540/451; 540/480; 540/597; 546/72
[58] Field of Search ............... 540/480, 597, 362, 451, 540/524; 546/72; 514/210, 212, 286

[56] References Cited

U.S. PATENT DOCUMENTS

| | | | |
|---|---|---|---|
| 3,509,158 | 4/1970 | Dobson et al. | 546/74 |
| 3,542,787 | 11/1970 | Dobson et al. | 546/74 |
| 3,597,433 | 8/1971 | Dobson et al. | 546/74 |
| 3,641,038 | 2/1972 | Davis et al. | 546/74 |
| 3,716,541 | 2/1973 | Dobson et al. | 546/74 |
| 3,717,641 | 2/1973 | Kocsis et al. | 546/74 |
| 3,892,756 | 7/1975 | Nedelec et al. | 546/74 |
| 4,009,273 | 2/1977 | Nedelec et al. | 546/72 |
| 4,052,508 | 10/1977 | Anderson etal. | 546/72 |
| 4,064,139 | 12/1977 | Anderson et al. | 546/72 |
| 4,232,158 | 11/1980 | Shepard et al. | 546/72 |
| 4,252,810 | 2/1981 | Anderson et al. | 546/72 |
| 4,374,838 | 2/1983 | Anderson et al. | 546/72 |
| 4,399,141 | 8/1983 | Anderson et al. | 546/72 |
| 4,414,154 | 11/1983 | Anderson et al. | 546/72 |
| 4,870,079 | 9/1989 | Britcher et al. | 514/289 |
| 4,940,789 | 7/1990 | Childers, Jr. et al. | 540/581 |
| 4,996,211 | 2/1991 | Baker et al. | 546/72 |
| 5,011,834 | 4/1991 | Weber et al. | 540/581 |

FOREIGN PATENT DOCUMENTS 0400916 12/1990 European Pat. Off. ............. 546/72

OTHER PUBLICATIONS

Monn et al. J. Med. Chem. 1990, 33 1069-1076.
Monn et al. Tetrahedron Letters 30(8) 911-914 1989.
Clineschmidt et al. Chemical Abstracts, vol. 97 1982, Abstract 16955d.
Rogawaski et al., "Anticonvulsant Activity of the Low-Affinity Uncompetitive N-Methyl—D-aspartate Antagonist ($\pm$)-5-Aminocarbonyl-10,11-dihydro-5-H-dibenzo[a,d]cyclohepten-5,10-imine (ADCl): Comparison with the Structural Analogs Dizocilpine (MK-801) and Carbamazepine," *J. Pharmacology and Experimental Therapeutics*, 259(1), 30-37 (1991).
Rogawski et al., "A Novel Anticonvulsant Structurally Related to the NMDA Antagonist MK-801 and to Carbamazepine," *Epilepsia*, 31, 620 (1990).
Yamaguchi et al., "Effects of Anticonvulsant Drugs on 4-Aminopyridine-Induced Seizures in Mice," *Epilepsy Res.*, 11, 9-16 (1992).
Coleman et al., "Protection Against Dendrotoxin-Induced Clonic Seizures in Mice by Anticonvulsant Drugs," *Brian Research*, 575, 138-142 (1992).
Novelli et al., "Glutamate Becomes Neurotoxic Via the N-methyl-D-aspartate Receptor When Intracellular Energy Levels Are Reduced," *Brain Research*, 45, 205-212 (1988).
Lysko et al., "Excitatory Aminco Acid Neurotoxicity at the N-methyl-D-aspartate Receptor in Cultured Neurons: Pharmacological Characterization," *Brain Research*, 499, 258-266 (1989).
Grant et al., "Comparison of the Effects of the Uncompetitive N-Methyl-D-Asparatate Antagonist ($\pm$)-5-Aminocarbonyl-10,11-Dihydro-5H-Dibenzo[a,d]cyclohepten-5,10-Imine (ADCL) with Its Structural Analogs Dizocilpine (MK-801) and Carbamazepine on Ethanol Withdrawal Seizures," *J. Pharmacology and Experimental Therapeutics*, 260(3), 1017-1022 (1992).
Rogawski et al., "Antiepileptic Drugs: Pharmacological Mechanisms and Clinical Efficacy with Consideration of Promising Development Stage Compounds," *Pharmacological Reviews*, 42(3), 223-286 (1990).

*Primary Examiner*—Robert T. Bond
*Assistant Examiner*—E. C. Ward
*Attorney, Agent, or Firm*—Leydig, Voit & Mayer

[57] ABSTRACT

This invention is in the field of clinical neurology and relates specifically to compounds, compositions and methods for treatment of patients with generalized epilepsy or partial (symptomatic) epilepsy using compounds of the formula:

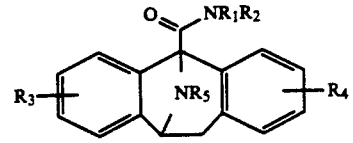

This invention also relates to compounds, compositions and methods of treatment for drug craving in patients addicted to cocaine.

12 Claims, No Drawings

5-AMINOCARBONYL-5H-DIBENZO[A,D]CYCLOHEPTEN-5,10-IMINES FOR TREATMENT OF EPILEPSY AND COCAINE ADDICTION

This application is a divisional of copending application Ser. No. 07/349,187, filed on May 9, 1989, now abandoned. The entire contents of which are hereby incorporated by reference.

FIELD OF THE INVENTION

This invention is in the field of clinical neurology and relates specifically to compounds, compositions and methods for treatment of patients with generalized epilepsy or partial (symptomatic) epilepsy. This invention also relates to compounds, compositions and methods of treatment for drug craving in patients addicted to cocaine.

BACKGROUND OF THE INVENTION

Epilepsy is a symptom of excessive temporary neuronal discharge, due to intracranial or extracranial causes; it is characterized clinically by discrete episodes, which tend to be recurrent, in which there is a disturbance of movement, behavior, perception and/or consciousness. The precise mechanism involved in the excessive neuronal discharge of epilepsy remains unknown. Nerve tissue is electronically excitable and this excitability is influenced by many factors. The relative tendency individuals to experience excessive neuronal discharge leading to seizures is referred to as the seizure threshold of the brain. In normal individuals possessing a high threshold and never experience abnormal periods of neuronal activity. Individuals with low threshold will periodically experience those episodes associated with epileptic seizures. The causes of the seizures may be from lowered neuronal resting potential due to inherent abnormalities in cellular ion gradients or in excitatory and inhibitory neuronal transmitter systems. Seizure spread may also be potentiated by damage to inhibitory neurons due to traumatic, infective, vascular or neoplastic causes. Hyperexcitability of neurons can also be a chronic effect caused by pyrexia, hypoxia, hypoglycemia, overhydration, alkalosis, withdrawal of barbiturates or alcoholism. In addition, seizures may be induced by convulsant drugs, electric shock, auditory or visual stimulus and physical and emotional stress.

Pharmaceutical agents used for the control of epilepsy fall into a variety of chemical classes including, but not limited to, acridines, amphetamines, barbiturates, carbamates, benzodiazepines, butyric acid derivatives, glutamic acid derivatives, valproic acid derivatives, ureas, hydantions, oxazolidinediones, succinimides, sulfonamides and hydrazones [see J. A. Vida, "Anticonvulsants", Academic Press, New York, 1977]. Convulsant seizures have been found to originate locally (at primary focii) in the brain and spread to other regions. The mode of action of most anticonvulsant drugs involves either the suppression of preconvulsant stimulus at the primary focus or inhibition of the spread of the excessive electrical activity to other brain regions [see. F. Morrell, W. Bradley and M. Ptashe, *Neurology*, 9,492 (1959)]. The majority of clinically useful anticonvulsant have a cyclic ureide structure.

cyclic ureide

These include the important drugs phenobarbital and diphenylhydantoin (Dilantin) Other clinically important which do not possess the cyclic ureide structure are primadone, benzodiazepines and carbamazepine.

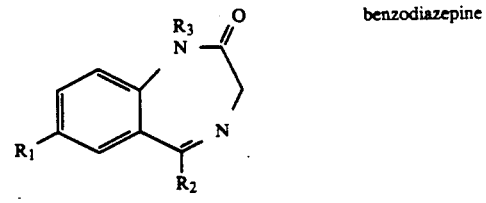

primidone

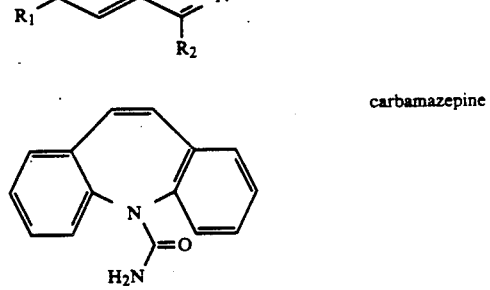

benzodiazepine

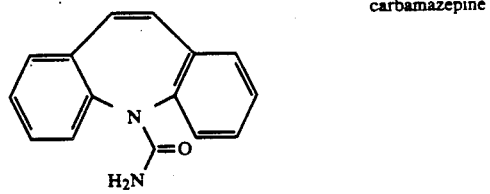

carbamazepine

Carbamazepine (5-carbamyl-5H-dibenzo[b,f]azepine) is a major anticonvulsant drug for the treatment of complex partial and generalized tonicclonic seizures. Carbamazepine is often used in patients who have not responded satisfactorily to treatment with other agents. It shows good activity and low acute and motor toxicity. Although it has been implicated in bone marrow suppression only one case of toxic overdose has been reported. The low toxicity of carbamazepine may be due to its low bioavailability.

Recent studies have indicated that carbamazepine may possess the ability to restrict cocaine craving in cocaine addicts. In one study 59% of the addicts taking the medication were able to abstain from cocaine for a prescribed period compared to 17% who received a placebo.

Recently, MK-801, a new anticonvulsant of novel structure, has shown potential usefulness for seizures of local origin and major generalized seizures. MK-801 is essentially free of the usual sedative side effects common to most of the commonly proscribed anticonvulsants [Clineschmidt et al *Drug Dev. Res*2, 123 (1982)]. Psychological disturbances in some of the patients in the clinical trials may be a consequence of the high affinity of the drug for phencyclidine binding sites in the central nervous system.

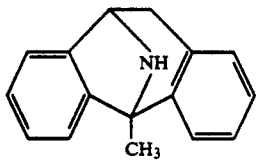

MK-801

DESCRIPTION OF THE INVENTION

Control of epileptic seizures and diminishment of drug craving in cocaine addicts is provided by treatment with an effective amount of a compound of the class of 5-aminocarbonyl-5H-dibenzo[a,d]cyclohepten-5,10-imines represented by Formula I:

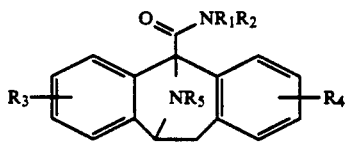

Formula 1 wherein each of $R_1$ and $R_2$ is independently selected from hydrido, linear or branched alkyl groups of from one to about twenty carbon atoms, alkenyl groups from two to about twenty carbon atoms, alkynyl groups from two to about twenty carbon atoms, cycloalkyl groups of three to about eight carbon atoms, cycloalkenyl groups from three to about eight carbon atoms, and wherein $R_1$ and $R_2$ may be taken together to form a N-containing cyclic structure having two to about eight carbon atoms, any of the said groups being optionally substituted with one or more substituents selected from alkyl, haloalkyl, hydroxyalkyl, alkenyl, oxo, hydroxyl, alkoxy, thio, alkoxyalkyl, amino, halo, cyano or mercapto, and wherein $R_3$ and $R_4$ is independently selected from hydrido, halo, linear or branched alkyl groups of from one to about ten carbon atoms, alkenyl groups from two to about ten carbon atoms, alkynyl groups from two to about ten carbon atoms, hydroxyl, amino, alkylamino, alkoxy, cyano, nitro, haloalkyl and mercapto, and wherein $R_5$ is selected from hydrido, linear or branched alkyl groups of from one to about ten carbon atoms, alkenyl groups from two to about ten carbon atoms, alkynyl groups from two to about ten carbon atoms, hydroxyl, phenyl, haloalkyl, aminoalkyl, 1-phenylmethyl, 2-phenylethyl and alkoxy, and wherein $R_1$ and $R_5$ taken together form a cyclic structure containing two nitrogen atoms possessing from two to about six carbon atoms, any of the said groups being optionally substituted by alkyl, oxo, thio, alkoxy, hydroxy, amino, alkylamino, phenyl, haloalkyl and thio; or a pharmaceutically acceptable salt thereof.

A preferred class of compounds within Formula I are those wherein each of $R_1$ and $R_2$ is independently selected from hydrido, alkyl, alkenyl, alkoxy or phenyl; wherein each of $R_3$ and $R_4$ is independently selected from hydrido, alkyl, alkenyl, halo, haloalkyl, hydroxy, alkoxy, nitro, cyano, thio, mercapto, amino, alkylamino, wherein $R_5$ is selected from hydrido, alkyl, alkenyl, haloalkyl, hydroxy, alkoxy, phenyl and aminoalkyl.

The term hydrido denotes a single hydrogen atom (H) which may be attached, for example, to a carbon atom or to a nitrogen atom to form a primary or secondary amino group. Where the term 'alkyl' is used, either alone or within other terms such as 'haloalkyl' or alkylamino' the term 'alkyl' embraces linear or branched radicals having one to about ten carbon atoms. Preferred alkyl radicals are "lower alkyl" radicals having from one to about five carbon atoms. The term 'cycloalkyl' embraces radicals having from three to about ten carbon atoms, such as cyclopropyl and cyclobutyl. The term "haloalkyl" embraces radicals wherein one or more of the alkyl carbon atoms is substituted with one or more halogens atoms, preferably selected from fluoro, chloro and bromo. Specifically embraced by the term 'haloalkyl' are monohaloalkyl, dihaloalkyl and polyhaloalkyl groups. Examples of a polyhaloalkyl are trifluoromethyl, 2,2,2-trifluoroethyl and perfluoroethyl. The term 'alkenyl' embraces linear or branched radicals having from two to about ten carbon atoms and containing at least one double bond. The term 'alkynyl' embraces linear or branched radicals having from two to about ten carbon atoms containing at least on carbon-carbon triple bond. The term 'alkoxy' embraces linear or branched oxy-containing radicals having alkyl portions of from one to about ten carbon atoms, such as methoxy group. The alkoxy radicals may be further substituted with one or more halo atoms, such as fluoro, chloro or bromo to provide haloalkoxy groups. The term 'alkylamino' embraces linear or branched nitrogen containing radicals where the nitrogen atom may be substituted with from one to three alkyl radicals of from one to about ten carbon atoms, such as N-methylamino and N,N-dimethylamino.

Specific examples of alkyl groups are methyl, ethyl, propyl, isopropyl, n-butyl, isobutyl, tert-butyl, sec-butyl, neopentyl and n-pentyl. Typical alkenyl groups may have one unsaturated double bond, such as allyl or may have a plurality of double bonds.

Included within the family of compounds of Formula I are the tautomeric forms of the described compounds, isomeric forms such as diastereomers, and the pharmaceutically acceptable salts thereof. Examples of acids which may be employed to form pharmaceutically acceptable acid addition salts include such inorganic acids as hydrochloric acid, sulphuric acid and phosphoric acid and such organic acids as maleic acid, succinic acid and citric acid.

Compounds of Formula 1 may be prepared in accordance with the following general procedures:

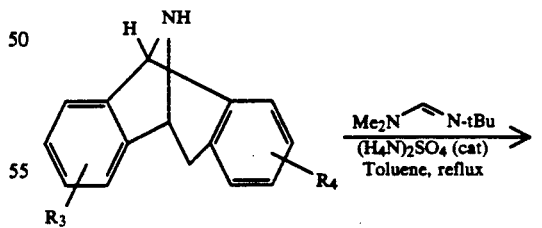

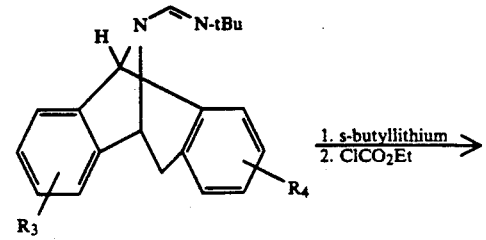

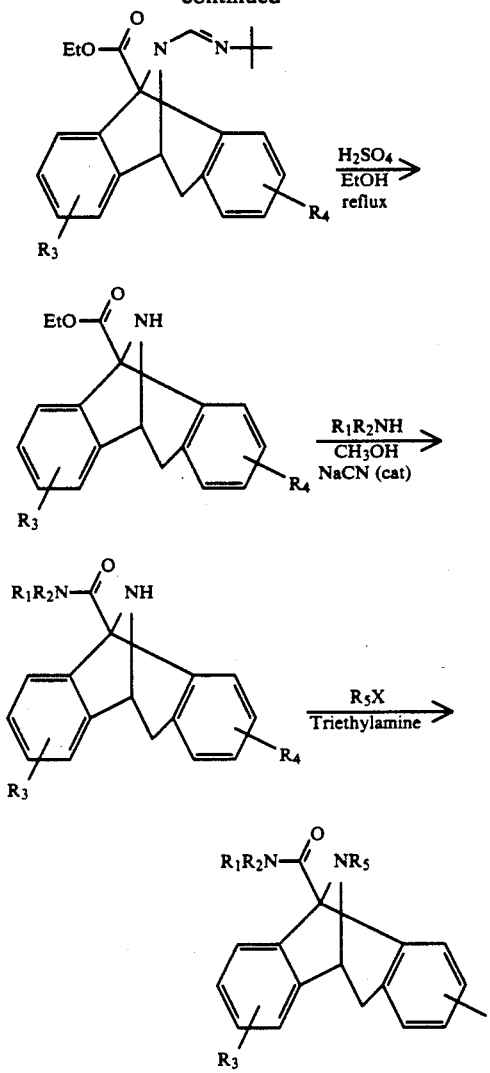

With reference to the foregoing scheme, the known and/or readily accessible racemic or optically active C5-unsubstituted-10,11-dihydro-5H-dibenzo[a,d]cyclohepten-5,10-imines are converted into their N-tert-butylformamidine derivatives. This is conveniently accomplished by reaction with a commercially available reagent, N'-tert-butyl-N,N-dimethylformamidine at elevated temperatures (110° C.) in the presence of an acid catalyst, generally ammonium sulfate. Secondly, the N-tert-butylformamidine derivatives in an anhydrous ethereal solvent at room temperature or at 5° C. are treated with sec-butyllithium followed by ethyl chloroformate. This results in the formation of the C5-substituted ethyl ester. The next step in the chemical sequence is the removal of the tert-butylformamidine moiety from the nitrogen atom of the parent ring system. This is achieved by heating in ethanolic sulfuric acid, and gives rise to 5-ethoxycarbonyl-10,11-dihydro-5H-dibenzo[a,d]cyclohepten-5,10-imines. The final step in the chemical synthesis is the replacement of ester functionality with an amide group. This is accomplished by warming the ester in methanol with the appropriate amine derivative. The presence of a catalytic amount of sodium cyanide facilites this reaction. If N-substitution is desired, the secondary amine is allowed to react with the appropriate alkyl halide in the presence of a suitable base (e.g. triethylamine).

EXAMPLE

Preparation of 5-Aminocarbonyl-10,11-dihydro-5H-dibenzo[a,d]cyclohepten-5,10-imine A mixture of 10,11-dihydro-5H-dibenzo[a,d]cyclohepten-5,10-imine (5.18 g, 25.0 mmol), N'-tert-butyl-N,N-dimethylformamidine (12.84 g, 100.0 mmol) and a few crystals of ammonium sulfate in anhydrous toluene was warmed under reflux for 6 days. Evaporation of the solvent and purification of the crude product by column chromatography employing 7% triethylamine in hexanes as the eluent afforded the N-tert-butylformamidinyl-10,11-dihydro-5H-dibenzo[a,d]cyclohepten-5,10-imine (6.98 g, 24.1 mmol, 96%): mp 63°-64°.

A solution of this material (5.80 g, 20.0 mmol) in anhydrous ethyl ether (150 mL) under an atmosphere of nitrogen was treated at 5° C. with a 1.25M solution of sec-butyllithium in cylohexane (20.0 mL, 25 mmol). The deep red colored solution of the anion was allowed to stir at this temperature for 40 minutes, then was treated with ethyl chloroformate (2.40 mL, 25.0 mmol). The solution color immediately changed to pale yellow, and gas chromatographic analysis of the reaction mixture demonstrated the complete consumption of the starting material. The reaction mixture was treated with ethanol (100 mL) and $H_2SO_4$ (0.56 mL, 10.0 mmol), and the ether was evaporated under reduced pressure. The ethanolic solution was warmed under reflux for 4 h, then was diluted with 0.5N HCl (100 mL) and extracted with $Et_2O$ (3×100). The aqueous part was made alkaline by addition 1N NaOH, and extracted with $Et_2O$ (3×100). The combined organic part was washed once with $H_2O$ (100 mL), then dried over $K_2CO_3$ and concentrated to dryness affording 5-ethoxycarbonyl-10,11-dihydro-5H-dibenzo[a,d]cyclohepten-5,10-imine (3.37 g, 12.1 mmol, 60%). The hydrogen chloride salt was formed by passing a stream of anhydrous HCl gas through an ethereal solution of the secondary amine: mp 229°-230° C.

A solution of the preceding amino ester (0.53 g, 1.90 mmol) and sodium cyanide (10 mg) in anhydrous methanol (40 mL) which had been previously saturated at 5° C. with ammonia gas was warmed to 60° C. in a sealed tube for 40 h. After cooling to 5° C., the solid which had formed was filtered, washed with $H_2O$, and air-dried affording 5-aminocarbonyl-10,11-dihydro-5H-dibenzo[a,d]cyclohepten-5,10-imine (0.25 g, 1.0 mmol). The filtrate was extracted with $CH_2Cl_2$ (3×50), the organic pool was dried ($K_2CO_3$) and evaporated under reduced pressure, affording an additional quantity of the title compound (0.19 g, 0.76 mmol). Recrystallization of the combined samples from ethanol then gave the analytically pure material (0.37 g, 1.5 mmol, 78%). mp 235°-236° C.

Table I is comprised of a list of 20 specific compounds of most

Table I is comprised of a list of 20 specific compounds of most interest within formula I. The preparation of compound 1 in Table I is described in detail in the previous example. Compounds 2 through 20 may likewise be prepared in accordance with the above-described general synthesis procedures.

TABLE 1

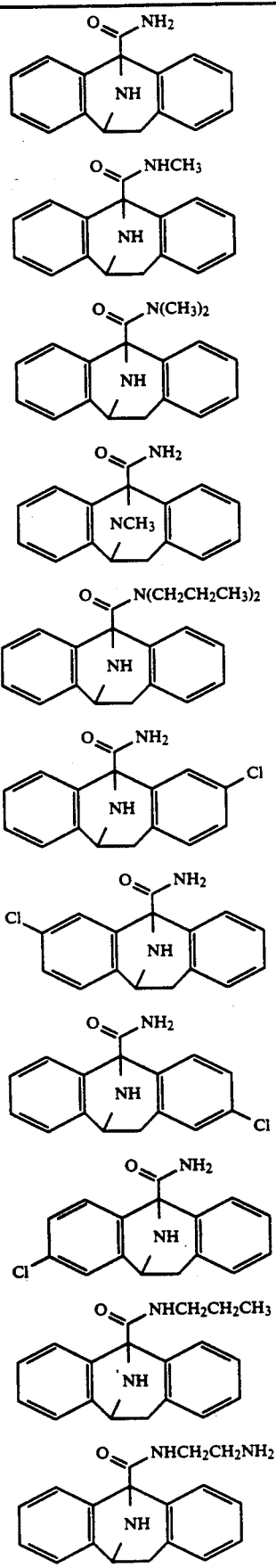

TABLE 1-continued

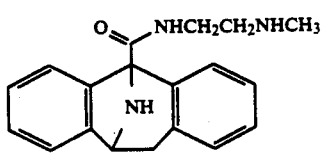

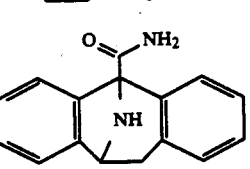

BIOLOGICAL EVALUATION

Compound 1 was administered intraperotoneally to male CF-1 type mice (20-25 g) with a saline solution carrier. The dose effect behavior was determined by the administration of six different doses of each compound, treating eight mice at each dose. After a period of fifteen minutes, the mice were subjected to corneal application of electroshock (30 mA at 50 Hz for 0.1 s). The ED$_{50}$ and the 95% confidence intervals of drug which eliminated the tonic-extensor component of the convulsion in 50% of the animals was calculated by the method of Litchfield and Wilcoxon (J. Pharmacol. Exp. Ther. 1949, 96, 99). Drug induced motor toxicity was examined using the inverted screen test which measures the ability of mice to hold onto a screen which has been turned vertical. Control animals will be able to hold on. Compound 1 showed an ED$_{50}$ for protection against maximal electroshock induced seizures of 8.9 mg/kg and a TD50 for motor toxicity of 50–55 mg/kg in mice. Thus compound 1 demonstrates a therapeutic index (TI) of 5.6–6.2.

Administration of compounds within Formula I to humans can be by any technique capable of introducing the compounds into the bloodstream of a human patient, including oral administration, and by intravenous, intramuscular and subcutaneous injections.

Compounds indicated by prophylactic therapy will preferably be administered in a daily dose generally in the range of 0.1 mg to 100 mg per kilogram of body weight per day. A more preferred dosage will be in the range of 1.0 to 50 mg per kilogram of body weight. A suitable dose can be administered in suitable sub-doses per day.

The active compound is usually administered in a pharmaceutically acceptable formulation, although in some acute-care situations a compound of Formula I may be administered alone. Such formulations may comprise the active compound with one or more pharmaceutically acceptable carriers or diluents. Other therapeutic agents may also be present in the formulation. A pharmaceutically acceptable carrier or diluent provides an appropriate vehicle for delivery of the active compound without undesirable side effects. Delivery of the active compound in such formulations may be by various routes such as oral, nasal, buccal or sublingual, or by parenteral administration such as subcutaneous, intramuscular, intravenous or intradermal routes. Delivery of the active compound may also be through the use of controlled release formulations in subcutaneous implants.

Formulations for oral administration may be in the form of capsules containing the active compound dispersed in a binder such as gelatin or hydroxypropylmethyl cellulose, together with one or more of a lubricant, preservative, surface acting or dispersing agent. Such capsules or tablets may contain controlled release formulation as may be provided in a disposition of active compound in hydroxypropylmethyl cellulose.

Formulations for parental administration may be in the form of aqueous or non-aqueous isotonic sterile injection solutions or suspensions. These solutions or suspensions may be prepared from sterile powders or granules having one or more of the carriers or diluents mentioned for use in the formulations for oral administration.

Although this invention has been described with respect to specific embodiments, the details of these embodiments are not to be construed as limitations. Various equivalents, changes and modifications may be made without departing from the spirit or scope of this invention, and it is understood that such equivalent embodiments are part of this invention.

What is claimed is:

1. A compound of the formula

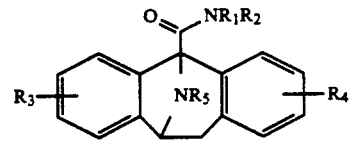

wherein each of $R_1$ and $R_2$ is independently selected from hydrogen, linear or branched alkyl groups of from one to twenty carbon atoms, alkenyl groups from two to twenty carbon atoms, alkynyl groups from two to twenty carbon atoms, cycloalkyl groups of three to eight carbon atoms, cycloalkenyl groups from three to eight carbon atoms, and wherein $R_1$ and $R_2$ may be taken together to form a N-containing cyclic structure having two to eight carbon atoms, any of the said groups being optionally substituted with one or more substituents selected from alkyl, haloalkyl, hydroxyalkyl, alkenyl, oxo, hydroxyl, alkoxy, thio, alkoxyalkyl, amino, halo, cyano or mercapto, and wherein $R_3$ and $R_4$ is independently selected from hydrogen, halo, linear or branched alkyl groups of from one to ten carbon atoms, alkenyl groups from two to ten carbon atoms, alkynyl groups from two to ten carbon atoms, hydroxyl, amino, alkylamino, alkoxy, cyano, nitro, haloalkyl and mercapto, and wherein $R_5$ is selected from hydrogen, linear or branched alkyl groups of from one to ten carbon atoms, alkenyl groups from two to ten carbon atoms, alkynyl groups from two to ten carbon atoms, hydroxyl, phenyl, haloalkyl, aminoalkyl, 1-phenylmethyl, 2-phenylethyl and alkoxy; or a pharmaceutically acceptable salt thereof.

2. A compound of claim 1 wherein each of $R_1$ and $R_2$ is independently selected from hydrogen, alkyl, alkenyl, alkoxy or phenyl; wherein each of $R_3$ and $R_4$ is independently selected from hydrogen, alkyl, alkenyl, halo, haloalkyl, hydroxy, alkoxy, nitro, cyano, thio, mercapto, amino, alkylamino, wherein $R_5$ is selected from hydrogen, alkyl, alkenyl, haloalkyl, hydroxy, alkoxy, phenyl and aminoalkyl.

3. A compound of claim 2 wherein each of $R_1$ and $R_2$ is independently selected from hydrogen, alkyl, alkenyl, and phenyl; wherein each of $R_3$ and $R_4$ is independently selected from hydrogen, alkyl, halo, haloalkyl, hydroxy, alkoxy, nitro, amino and alkylamino, wherein $R_5$ is selected from hydrogen, alkyl, alkenyl, haloalkyl, hydroxy, alkoxy, phenyl and aminoalkyl.

4. A compound of claim 3 which is 5-aminocarbonyl-5H-dibenzo[a,d]cyclohepten-5,10-imine.

5. A pharmaceutical composition comprising a therapeutically effective amount of a compound to treat or prevent epileptic seizures and a pharmaceutically-acceptable carrier or diluent, said compound having the formula

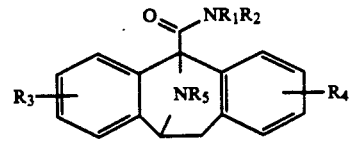

wherein each of $R_1$ and $R_2$ is independently selected from hydrogen, linear or branched alkyl groups of from one to twenty carbon atoms, alkenyl groups from two to twenty carbon atoms, alkynyl groups from two to twenty carbon atoms, cycloalkyl groups of three to eight carbon atoms, cycloalkenyl groups from three to eight carbon atoms, and wherein $R_1$ and $R_2$ may be taken together to form a N-containing cyclic structure having two to eight carbon atoms, any of the said groups being optionally substituted with one or more substituents selected from alkyl, haloalkyl, hydroxyalkyl, alkenyl, oxo, hydroxyl, alkoxy, thio, alkoxyalkyl, amino, halo, cyano or mercapto, and wherein $R_3$ and $R_4$ is independently selected from hydrogen, halo, linear or branched alkyl groups of from one to ten carbon atoms, alkenyl groups from two to ten carbon atoms, alkynyl groups from two to ten carbon atoms, hydroxyl, amino, alkylamino, alkoxy, cyano, nitro, haloalkyl and mercapto, and wherein $R_5$ is selected from hydrogen, linear or branched alkyl groups of from one to ten carbon atoms, alkenyl groups from two to ten carbon atoms, alkynyl groups from two to ten carbon atoms, hydroxyl, phenyl, haloalkyl, aminoalkyl, 1-phenylmethyl, 2-phenylethyl and alkoxy; or a pharmaceutically acceptable salt thereof.

6. A composition of claim 5 wherein each of $R_1$ and $R_2$ is independently selected from hydrogen, alkyl, alkenyl, alkoxy or phenyl; wherein each of $R_3$ and $R_4$ is independently selected from hydrogen, alkyl, alkenyl, halo, haloalkyl, hydroxy, alkoxy, nitro, cyano, thio, mercapto, amino, alkylamino, wherein $R_5$ is selected from hydrogen, alkyl, alkenyl, haloalkyl, hydroxy, alkoxy, phenyl and aminoalkyl.

7. A composition of claim 6 wherein each of $R_1$ and $R_2$ is independently selected from hydrogen, alkyl, alkenyl, and phenyl; wherein each of $R_3$ and $R_4$ is independently selected from hydrogen, alkyl, halo, haloalkyl, hydroxy, alkoxy, nitro, amino and alkylamino, wherein $R_5$ is selected from hydrogen, alkyl, alkenyl, haloalkyl, hydroxy, alkoxy, phenyl and aminoalkyl.

8. A composition of claim 7 which is 5-aminocarbonyl-5-H-dibenzo[a,d]cyclohepten-5,10-imine.

9. A method to treat and control epileptic seizures in mammals, which method comprises treating a mammal susceptible to epileptic seizures with an effective amount of a compound of the formula

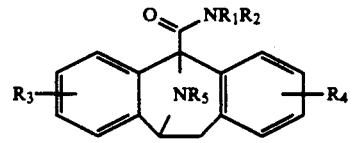

wherein each of $R_1$ and $R_2$ is independently selected from hydrogen, linear or branched alkyl groups of from one to twenty carbon atoms, alkenyl groups from two to twenty carbon atoms, alkynyl groups from two to twenty carbon atoms, cycloalkyl groups of three to eight carbon atoms, cycloalkenyl groups from three to eight carbon atoms, and wherein $R_1$ and $R_2$ may be taken together to form a N-containing cyclic structure having two to eight carbon atoms, any of the said groups being optionally substituted with one or more substituents selected from alkyl, haloalkyl, hydroxyalkyl, alkenyl, oxo, hydroxyl, alkoxy, thio, alkoxyalkyl, amino, halo, cyano or mercapto, and wherein $R_3$ and $R_4$ is independently selected from hydrogen, halo, linear or branched alkyl groups of from one to ten carbon atoms, alkenyl groups from two to ten carbon atoms, alkynyl groups from two to ten carbon atoms, hydroxyl, amino, alkylamino, alkoxy, cyano, nitro, haloalkyl and mercapto, and wherein $R_5$ is selected from hydrogen, linear or branched alkyl groups of from one to ten carbon atoms, alkenyl groups from two to ten carbon atoms, alkynyl groups from two to ten carbon atoms, hydroxyl, phenyl, haloalkyl, aminoalkyl, 1-phenylmethyl, 2-phenylethyl and alkoxy; or a pharmaceutically acceptable salt thereof.

10. The method of claim 9 wherein each of $R_1$ and $R_2$ is independently selected from hydrogen, alkyl, alkenyl, alkoxy or phenyl; wherein each of $R_3$ and $R_4$ is independently selected from hydrogen, alkyl, alkenyl, halo, haloalkyl, hydroxy, alkoxy, nitro, cyano, thio, mercapto, amino, alkylamino, wherein $R_5$ is selected from hydrogen, alkyl, alkenyl, haloalkyl, hydroxy, alkoxy, phenyl and aminoalkyl.

11. The method of claim 10 wherein each of $R_1$ and $R_2$ is independently selected from hydrogen, alkyl, alkenyl, and phenyl; wherein each of $R_3$ and $R_4$ is independently selected from hydrogen, alkyl, halo, haloalkyl, hydroxy, alkoxy, nitro, amino and alkylamino, wherein $R_5$ is selected from hydrogen, alkyl, alkenyl, haloalkyl, hydroxy, alkoxy, phenyl and aminoalkyl.

12. The method of claim 11 which is 5-aminocarbonyl-5-H-dibenzo[a,d]cyclohepten-5,10-imine.

* * * * *